(12) United States Patent
Saigusa et al.

(10) Patent No.: US 11,166,693 B2
(45) Date of Patent: Nov. 9, 2021

(54) RADIATION IMAGING SYSTEM, CONTROL METHOD OF RADIATION IMAGING SYSTEM AND NON-TRANSITORY COMPUTER-READABLE STORAGE MEDIUM

(71) Applicant: CANON KABUSHIKI KAISHA, Tokyo (JP)

(72) Inventors: Akio Saigusa, Tama (JP); Akiya Nakayama, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 99 days.

(21) Appl. No.: 16/750,716

(22) Filed: Jan. 23, 2020

(65) Prior Publication Data

US 2020/0155108 A1    May 21, 2020

Related U.S. Application Data

(63) Continuation of application No. PCT/JP2018/025491, filed on Jul. 5, 2018.

(30) Foreign Application Priority Data

Sep. 22, 2017  (JP) .............................. JP2017-182948

(51) Int. Cl.
*G01N 23/04* (2018.01)
*A61B 6/00* (2006.01)

(52) U.S. Cl.
CPC ............ *A61B 6/542* (2013.01); *A61B 6/4208* (2013.01); *G01N 23/04* (2013.01)

(58) Field of Classification Search
CPC ....... A61B 6/542; A61B 6/4208; G01N 12/04
See application file for complete search history.

(56) References Cited

U.S. PATENT DOCUMENTS 7,196,725 B1    3/2007  Saigusa et al.
7,856,085 B2   12/2010  Hayashida
(Continued)

FOREIGN PATENT DOCUMENTS

JP    2006-333898    12/2006
JP    2010-035778     2/2010
(Continued)

OTHER PUBLICATIONS

U.S. Appl. No. 16/720,833, Akio Saigusa, filed Dec. 19, 2020.

*Primary Examiner* — David P Porta
*Assistant Examiner* — Djura Malevic
(74) *Attorney, Agent, or Firm* — Venable LLP

(57) ABSTRACT

A radiation imaging system is provided. The system comprises: an imaging unit including a plurality of pixels configured to generate a radiation image and a detection unit configured to detect incident radiation to perform exposure control; an irradiation control unit configured to control radiation irradiation by a radiation source, an obtainment unit configured to obtain a delay time of communication between the imaging unit and the irradiation control unit; and a determination unit. The determination unit determines, based on a radiation irradiation condition set by an operator and the delay time obtained by the obtainment unit, whether to permit imaging by exposure control using a signal output from the detection unit.

18 Claims, 8 Drawing Sheets

(56) References Cited

U.S. PATENT DOCUMENTS

| | | | |
|---|---|---|---|
| 8,969,820 B2 | 3/2015 | Suwa et al. | |
| 9,052,400 B2 | 6/2015 | Saruta et al. | |
| 9,078,624 B2* | 7/2015 | Sugizaki | G01T 1/2928 |
| 9,492,137 B2* | 11/2016 | Iwamoto | A61B 6/4405 |
| 9,788,809 B2* | 10/2017 | Hiroike | A61B 6/54 |
| 10,022,102 B2 | 7/2018 | Okada | |
| 10,682,105 B2* | 6/2020 | Shimizukawa | A61B 6/54 |
| 10,736,597 B2* | 8/2020 | Yachi | A61B 6/548 |
| 2001/0041832 A1* | 11/2001 | Hirai | A61B 6/06 600/407 |
| 2003/0086523 A1* | 5/2003 | Tashiro | A61B 6/4233 378/19 |
| 2004/0258204 A1* | 12/2004 | Nokita | A61B 6/585 378/91 |
| 2010/0207032 A1* | 8/2010 | Tsubota | G01T 1/17 250/370.09 |
| 2012/0018641 A1* | 1/2012 | Watanabe | A61B 6/563 250/354.1 |
| 2013/0136234 A1* | 5/2013 | Noma | H05G 1/64 378/91 |
| 2013/0148782 A1* | 6/2013 | Tajima | A61B 6/4233 378/62 |
| 2013/0148784 A1 | 6/2013 | Tajima | |
| 2013/0153775 A1 | 6/2013 | Nomura et al. | |
| 2013/0208860 A1* | 8/2013 | Sugizaki | A61B 6/542 378/62 |
| 2014/0072103 A1* | 3/2014 | Kitano | A61B 6/4233 378/62 |
| 2014/0091225 A1 | 4/2014 | Sasaki et al. | |
| 2014/0151769 A1 | 6/2014 | Wayama et al. | |
| 2014/0254760 A1* | 9/2014 | Hiroike | A61B 6/4233 378/62 |
| 2018/0353150 A1* | 12/2018 | Takeshima | A61B 6/54 |

FOREIGN PATENT DOCUMENTS

| | | |
|---|---|---|
| JP | 2013-138829 | 7/2013 |
| JP | 2013-162963 | 8/2013 |
| JP | 2015-083114 | 4/2015 |
| JP | 2017-094010 | 6/2017 |
| WO | 2013/176251 | 11/2013 |

* cited by examiner

F I G. 6

| IMAGING PART | VOLTAGE [kV] | CURRENT [mA] | IRRADIATION TIME [ms] | mAs VALUE | SID [cm] | COMMUNICATION DELAY THRESHOLD [ms] |
|---|---|---|---|---|---|---|
| CHEST PA | 130 | 300 | 10 | 3.0 | 200 | 0.5 |
| SIDE OF CHEST | 130 | 300 | 30 | 9.0 | 200 | 0.5 |
| FRONT OF ABDOMEN | 80 | 300 | 120 | 36.0 | 150 | 6 |
| SIDE OF ABDOMEN | 80 | 300 | 200 | 72.0 | 150 | 10 |
| FOUR LIMBS | 70 | 150 | 50 | 7.5 | 120 | 2.5 |

RADIATION IMAGING SYSTEM, CONTROL METHOD OF RADIATION IMAGING SYSTEM AND NON-TRANSITORY COMPUTER-READABLE STORAGE MEDIUM

CROSS-REFERENCE TO RELATED APPLICATIONS

This application is a Continuation of International Patent Application No. PCT/JP2018/025491, filed Jul. 5, 2018, which claims the benefit of Japanese Patent Application No. 2017-182948, filed Sep. 22, 2017, both of which are hereby incorporated by reference herein in their entirety.

BACKGROUND OF THE INVENTION

Field of the Invention

The present invention relates to a radiation imaging system, a control method of the radiation imaging system, and a non-transitory computer-readable storage medium.

Background Art

In medical image diagnosis and nondestructive inspection, a radiation imaging apparatus that uses a flat panel detector (FPD) made of a semiconductor material is widely used. In such a radiation imaging apparatus, it is known that monitoring of radiation which enters the radiation imaging apparatus is performed. Detecting the radiation dose in real time allows automatic exposure control (AEC) to be performed by detecting the start and the end of the radiation irradiation and grasping the cumulative dose of radiation that entered the radiation imaging apparatus during radiation irradiation. PTL 1 shows that signals for AEC are exchanged between a radiation imaging apparatus and a control apparatus by wireless communication.

CITATION LIST

Patent Literature

PTL 1: Japanese Patent Laid-Open No. 2013-162963

A wireless communication environment will change greatly due to noise generated together with the operation of other wireless communication devices or other medical devices such as a microwave therapy device and the like. That is, the wireless communication environment is not constantly stable, and an unstable state such as frequent disconnection due to noise generated in the periphery, reduced communication data rate, or the like can occur. Also, even in a wired communication environment, the communication rate may degrade in a case in which a device such as a switching hub is interposed between communication paths or in a case in which the communication amount increases in the same network.

In a radiation imaging system that performs AEC, radiation irradiation cannot be stopped at a suitable timing if the communication delay time increases, and this may cause excessive radiation irradiation to be performed within the range of the maximum irradiation time set by an operator.

An object of the present invention is to provide a technique advantageous in improving the controllability of AEC in a radiation imaging system.

SUMMARY OF THE INVENTION

According to some embodiments, a radiation imaging system comprising: an imaging unit including a plurality of pixels configured to generate a radiation image and a detection unit configured to detect incident radiation to perform exposure control; an irradiation control unit configured to control radiation irradiation by a radiation source, an obtainment unit configured to obtain a delay time of communication between the imaging unit and the irradiation control unit; and a determination unit, wherein the determination unit determines, based on a radiation irradiation condition set by an operator and the delay time obtained by the obtainment unit, whether to permit imaging by exposure control using a signal output from the detection unit, is provided.

According to some other embodiments, a control method of a radiation imaging system that includes an imaging unit including a plurality of pixels configured to generate a radiation image and a detection unit configured to detect incident radiation to perform exposure control, an irradiation control unit configured to control radiation irradiation by a radiation source, and an obtainment unit configured to obtain a delay time of communication between the imaging unit and the irradiation control unit, the control method comprising: a step of determining, based on a radiation irradiation condition set by an operator and the delay time obtained by the obtainment unit, whether to permit imaging by exposure control using a signal output from the detection unit, is provided.

According to still other embodiments, a non-transitory computer-readable storage medium storing a program for causing a computer to execute a control method of a radiation imaging system that includes an imaging unit including a plurality of pixels configured to generate a radiation image and a detection unit configured to detect incident radiation to perform exposure control, an irradiation control unit configured to control radiation irradiation by a radiation source, and an obtainment unit configured to obtain a delay time of communication between the imaging unit and the irradiation control unit, the control method comprising: a step of determining, based on a radiation irradiation condition set by an operator and the delay time obtained by the obtainment unit, whether to permit imaging by exposure control using a signal output from the detection unit, is provided.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 6 is a table showing an example of combinations of irradiation conditions of the radiation imaging system of FIG. 1;

DESCRIPTION OF THE EMBODIMENTS

Detailed embodiments of a radiation imaging system according to the present invention will be described hereinafter with reference to the accompanying drawings. Note that radiation according to the present invention can include not only α-rays, β-rays, and γ-rays that are beams generated by particles (including photons) emitted by radioactive decay, but also beams that have equal or more energy, for example, X-rays, particle rays, and cosmic rays.

Figure 1:
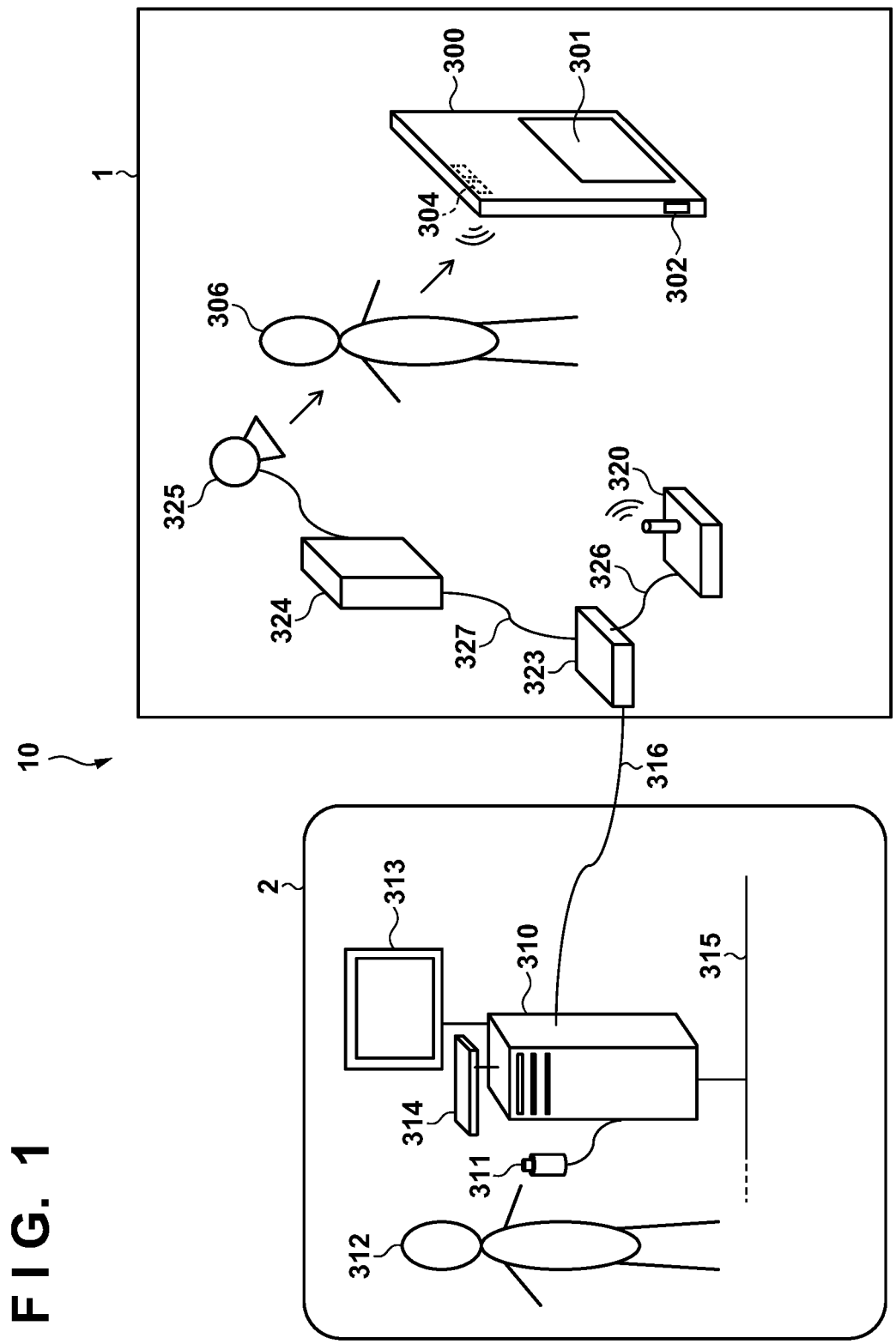
FIG. 1 is a view showing an example of the arrangement of a radiation imaging system according to an embodiment of the present invention.

An arrangement and a control method of a radiation imaging system according to an embodiment of the present invention will be described with reference to FIGS. 1 to 6. FIG. 1 is a view showing an example of the arrangement of a radiation imaging system 10 according to the first embodiment of the present invention. As shown in FIG. 1, the radiation imaging system 10 is arranged in a radiation room 1 for irradiating a subject with radiation and performing radiation imaging and a control room 2 for an operator 312 to control each component arranged in the radiation room 1.

The radiation room 1 includes an imaging unit 300, an access point 320, a communication control unit 323, an irradiation control unit 324, and a radiation source 325 of the radiation imaging system 10. The radiation room 1 also includes an access point (AP) communication cable 326 and an irradiation control unit communication cable 327. The control room 2 includes a system control unit 310, a radiation irradiation switch 311, a display unit 313, an input unit 314, an in-hospital LAN (local area network) 315, and a room-to-room communication cable 316 of the radiation imaging system 10.

The imaging unit 300 includes a wireless communication unit 304 and a power supply control unit 301 which is formed by a battery or the like. The imaging unit 300 can also include a wired communication unit 302. The imaging unit 300 can also be called a radiation imaging apparatus. The imaging unit 300 generates radiation image data by detecting the radiation emitted from the radiation source 325 and passed through a subject 306.

The access point 320 performs wireless communication with the imaging unit 300. In this embodiment, the access point 320 is used to relay the communication between the imaging unit 300, the system control unit 310, and the irradiation control unit 324.

The communication control unit 323 performs control so that the imaging unit 300, the irradiation control unit 324, and the system control unit 310 can communicate with each other via the access point 320.

The irradiation control unit 324 controls the radiation source 325 so that the radiation source 325 can perform radiation irradiation based on a predetermined imaging condition. The radiation source 325 performs radiation irradiation under the control of the irradiation control unit 324.

The access point communication cable 326 is a cable for connecting the access point 320 and the communication control unit 323. The irradiation control unit communication cable 327 is a cable for connecting the irradiation control unit 324 and the communication control unit 323.

The system control unit 310 communicates with the irradiation control unit 324 and the imaging unit 300 via the communication control unit 323 to control the overall radiation imaging system 10. The radiation irradiation switch 311 is a switch for the operator 312 to make an operation to input the timing of radiation irradiation. The input unit 314 is a device for the operator 312 to input an instruction to the radiation imaging system 10. Various kinds of input devices such as a keyboard, a touch panel, and the like can be used as the input unit 314. The display unit 313 is a device that displays a GUI (Graphical User Interface) and radiation image data which has undergone image processing. A display or the like is used as the display unit 313. The in-hospital LAN 315 is the main network used in a hospital and is connected to an HIS (Hospital Information System), an RIS (Radiology Information System), or the like. The room-to-room communication cable 316 is a cable used to connect the system control unit 310 and the communication control unit 323 which is arranged in the radiation room 1.

The operation of the radiation imaging system 10 will be described next. First, the operator 312 inputs subject information such as the ID, the name, and the birthday of the subject 306 and imaging information such as the imaging part of the subject 306 in the system control unit 310. Other than directly inputting and setting the subject information and the imaging information from the input unit 314 or the like, the subject information and the imaging information can be automatically set by selecting an inspection order received via the in-hospital LAN 315. Also, the information of the imaging part can be set by selecting a preset imaging protocol.

After the subject information and the imaging information have been input, the operator 312 will fix the orientation of the subject 306 and the imaging unit 300 at predetermined positions.

After completing the imaging preparation by inputting the subject information and the imaging information and positioning the subject 306 and the imaging unit 300, the operator 312 presses the radiation irradiation switch 311. When the radiation irradiation switch 311 is pressed, a signal for radiation irradiation is transmitted to the radiation source from the system control unit 310 via the irradiation control unit 324. The radiation source 325 performs radiation irradiation, in accordance with the signal for radiation irradiation, based on the irradiation conditions corresponding to the imaging conditions input by the operator 312.

The radiation emitted on the subject 306 passes through the subject 306 and enters the imaging unit 300. The imaging unit 300 detects the incident radiation as a radiation image signal. The imaging unit 300 can communicate with the system control unit 310 and the irradiation control unit 324 to control the start and the end of radiation irradiation by performing automatic exposure control (AEC) corresponding to the incident radiation dose. Imaging using AEC will be described later.

The imaging unit 300 reads out each detected radiation image signal and causes the AD conversion circuit to convert the detected analog radiation image signal into a digital signal to obtain radiation image data based on digital data. The obtained radiation image data is transferred from the imaging unit 300 to the system control unit 310.

The system control unit 310 performs image processing on the received radiation image data. The system control unit 310 causes the display unit 313 to display the radiation image based on the radiation image data that have undergone image processing. In this embodiment, the system control unit 310 may function as an image processing device and a display control device in this manner. Also, the radiation imaging system 10 may include, separately from the system control unit 310, another arrangement to control image processing and the display on the display unit 313.

Figure 2:
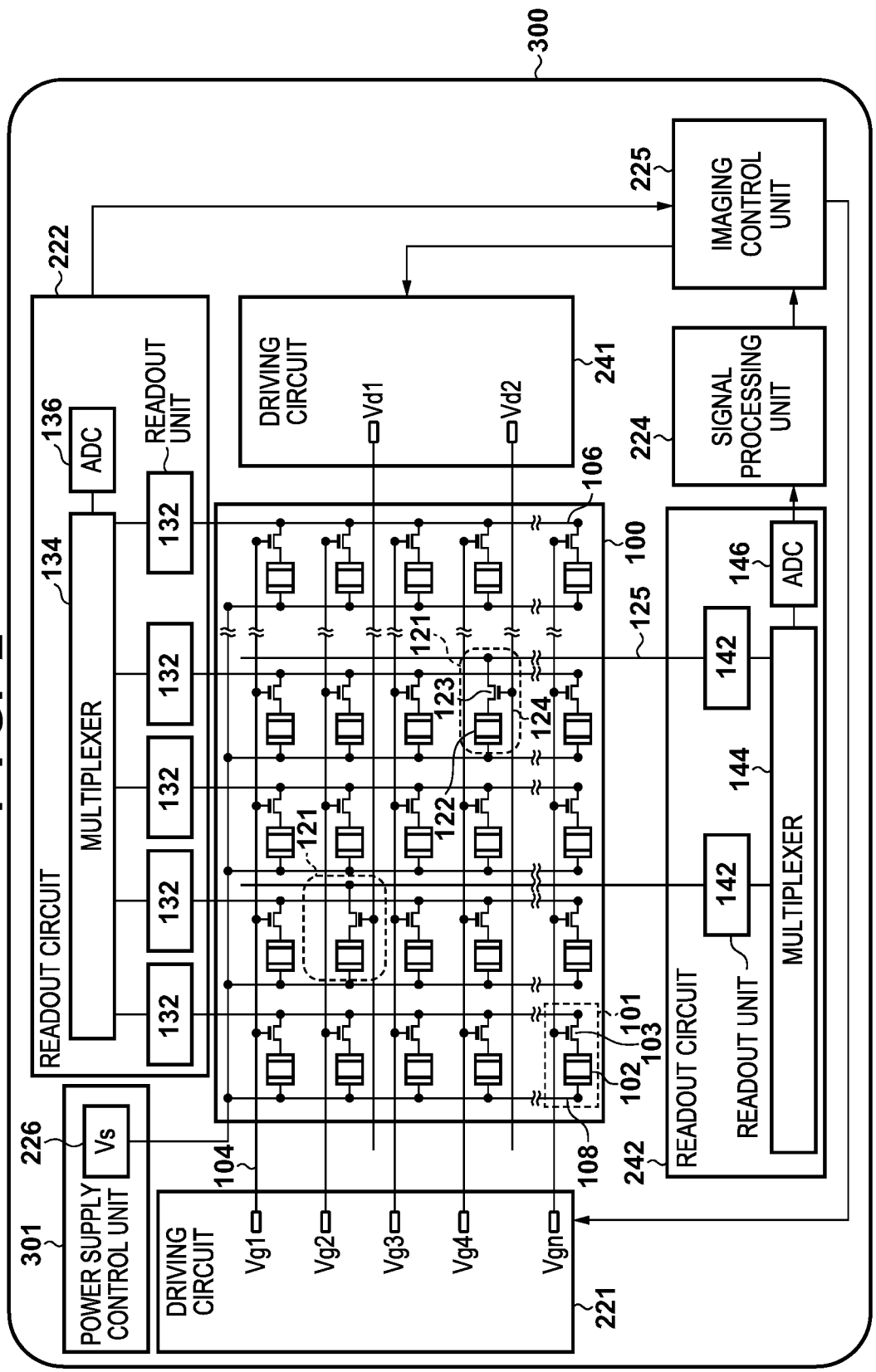
FIG. 2 is a block diagram showing an example of the arrangement of an imaging unit of the radiation imaging system of FIG. 1.

The imaging unit 300 will be described next. FIG. 2 is a block diagram showing an example of the arrangement of the imaging unit 300. As shown in FIG. 2, the imaging unit 300 includes a pixel region 100 arranged with a plurality of pixels 101 and 121 so as to form a plurality of rows and a plurality of columns. That is, the pixel region 100 includes a function to detect the radiation emitted on the pixel region 100. In this embodiment, the pixels 101 and 121 include the pixels 101 for generating a radiation image and the pixels 121 for monitoring the radiation irradiation and performing exposure control (AEC). Each pixel 121 is a detection unit that detects incident radiation to perform exposure control.

In this embodiment, as will be described later, even if the pixels 101 and 121 are arranged in the same column, the pixels 101 and 121 will output signals to different readout units 132 and 142, respectively, and the functions of the pixels 101 and 121 are divided between the radiation image generation function and the radiation monitoring function (detection unit). However, the present invention is not limited to this. It may be set so that only the pixels 101 will be arranged in the pixel region and an arbitrarily selected pixel 101 of the pixels 101 will function as the detection unit. In addition, the detection unit may be arranged in the pixel region 100 as in the arrangement shown in FIG. 2 or may be arranged outside the pixel region 100. In a case in which each detection unit is to be arranged outside the pixel region 100, the detection unit may be arranged in the imaging unit 300 in a portion other than the pixel region 100 or, for example, be arranged adjacently to the imaging unit 300 so as to be independent of the imaging unit 300.

Each pixel 101 includes a conversion element 102 that converts radiation into an electric signal and a switch element 103 arranged between the conversion element 102 and a corresponding column signal line 106. Each pixel 121 includes a conversion element 122 that converts radiation into an electric signal and a switch element 123 arranged between the conversion element 122 and a corresponding detection signal line 125. The pixel 121 is arranged in the same column as some of the plurality of pixels 101.

The conversion element 102 and the conversion element 122 can include a scintillator that converts radiation into light and a photoelectric conversion element that converts light into an electric signal. In general, the scintillator is formed to be like a sheet so as to cover the pixel region 100 and is shared by the plurality of pixels 101 and 121. Each of the conversion elements 102 and the conversion elements 122 can also be formed by a conversion element that directly converts radiation into an electric signal. Each of the switch elements 103 and the switch elements 123 can be, for example, a thin film transistor (TFT) in which an active region made of a semiconductor such as amorphous silicon, polysilicon, or the like has been formed.

In addition, the imaging unit 300 includes the plurality of column signal lines 106 and a plurality of driving lines 104. Each column signal line 106 corresponds to a column of the plurality of columns of the pixel region 100. Each driving line 104 corresponds to a row of the plurality of rows of the pixel region 100. Each driving line 104 is driven by a driving circuit 221.

A first electrode of the conversion element 102 is connected to a first main electrode of the switch element 103, and a second electrode of the conversion element 102 is connected to a corresponding bias line 108. Each bias line 108 extends in the column direction and is connected commonly to the second electrodes of the plurality of conversion elements 102 arranged in the column direction.

The bias line 108 receives a bias voltage Vs which is supplied from an element power supply circuit 226. The power supply control unit 301 is formed by a battery, DCDC converter, and the like. The power supply control unit 301 includes the element power supply circuit 226 and generates an analog circuit power supply voltage and a digital circuit power supply voltage, which is used for drive control, wireless communication, and the like.

The second main electrodes of the switch elements 103 of the plurality of pixels 101 that form one column are connected to the column signal line 106 in common. The control electrodes of the switch element 103 of the plurality of pixels 101 that form one row are connected to the driving line 104 in common. The plurality of column signal lines 106 are connected to a readout circuit 222. The readout circuit 222 here includes the plurality of readout units 132, a multiplexer 134, and an analog/digital (AD) converter 136.

Each of the plurality of column signal lines 106 is connected to the readout unit 132 corresponding to each column among the plurality of readout units 132 of the readout circuit 222. One column signal line 106 corresponds to one readout unit 132. The readout unit 132 includes, for example, a differential amplifier. The multiplexer 134 selects the plurality of readout units 132 in a predetermined order and supplies a signal from the selected readout unit 132 to the AD converter 136. The AD converter 136 converts the supplied signal into a digital signal and outputs the converted digital signal.

A first electrode of the conversion element 122 is connected to a first main electrode of the switch element 123, and a second electrode of the conversion element 122 is connected to the corresponding bias line 108. A second main electrode of the switch element 123 is connected to the corresponding detection signal line 125. A control electrode of the switch element 123 is electrically connected to a corresponding driving line 124.

The imaging unit 300 includes the plurality of detection signal lines 125. One or a plurality of pixels 121 serving as detection units are connected to one detection signal line 125. Each driving line 124 is driven by a driving circuit 241. One or a plurality of pixels 121 are connected to one driving line 124. The detection signal lines 125 are connected to a readout circuit 242. The readout circuit 242 includes the plurality of readout units 142, a multiplexer 144, and an AD converter 146.

Each of the plurality of detection signal lines 125 is connected to the corresponding readout unit 142 among the plurality of readout units 142 of the readout circuit 242. One detection signal line 125 is connected to one readout unit 142. Each readout unit 142 includes, for example, a differential amplifier. The multiplexer 144 selects the plurality of readout units 142 in a predetermined order and supplies a signal from the selected readout unit 142 to the AD converter 146. The AD converter 146 converts the supplied signal into a digital signal and outputs the converted digital signal. The output from the readout circuit 242 (the AD converter 146) is supplied to a signal processing unit 224 and processed by the signal processing unit 224. The signal processing unit 224 outputs, based on the output from the readout circuit 242 (the AD converter 146), information indicating the radiation irradiation performed on the imaging unit 300. More specifically, for example, the signal processing unit 224 detects the start of radiation irradiation to the imaging unit 300, detects the incident radiation dose, or calculates the cumulative irradiation dose.

An imaging control unit 225 controls the driving circuit 221, the driving circuit 241, the readout circuits 222 and 242, and the like based on the information from the signal processing unit 224 and each control command from the system control unit 310.

An exposure (dose) control operation of the radiation imaging system 10 performed by using the imaging unit 300 will be described next. The operator 312 inputs, to the system control unit 310, irradiation conditions such as the dose, the maximum irradiation time, the tube current, the tube voltage, the mAs value (tube current-time product), and the like and imaging information such as the radiation detection region (ROI) which is a region in which the radiation is to be monitored, the imaging part, and the like. The irradiation conditions may be set automatically from the data, which is stored in the storage unit of the system control unit 310, based on the imaging part, the subject information, and the like. In addition, the imaging information may be set automatically by selecting an inspection order received from the in-hospital LAN as described above. The system control unit 310 transmits the input radiation irradiation conditions, the radiation detection region (ROI), the portion information, and the like to the imaging unit 300 and the irradiation control unit 324.

After the imaging preparation has been completed and radiation irradiation switch 311 is pressed by the operator 312, radiation is emitted from the radiation source 325. The emitted radiation passes through the subject 306 and enters the imaging unit 300. The imaging unit 300 detects the radiation that entered the radiation detection region (ROI) by using each pixel 121 functioning as a detection unit, and calculates the cumulative irradiation dose which is a cumulative value of the dose (total dose) detected for a predetermined period by the signal processing unit 224. The imaging control unit 225 calculates the appropriate dose based on the information of the cumulative irradiation dose transmitted from the signal processing unit 224 and the portion information and the irradiation conditions input by the operator 312, and performs exposure control (AEC) that determines the radiation irradiation stop timing. Based on the determined radiation irradiation stop timing, the imaging control unit 225 of the imaging unit 300 notifies the irradiation control unit 324 of the stop via the access point 320 and the communication control unit 323. The irradiation control unit 324 causes the radiation source 325 to stop the radiation irradiation based on the radiation irradiation stop timing of the notification. Although the imaging unit 300 has transmitted a radiation irradiation stop notification as a radiation detection result to the irradiation control unit, the present invention is not limited to this. It may be arranged so that the imaging unit 300 will transmit the total dose as a detection result to the irradiation control unit 324 for each predetermined time and the irradiation control unit 324 will calculate the cumulative value of the total doses. In addition, it may be arranged so that the imaging unit 300 will transmit the total dose to the system control unit 310 for each predetermined time, the system control unit 310 will calculate the cumulative value of the total doses, and the system control unit 310 will transmit a notification to the irradiation control unit 324 to stop the radiation irradiation operation. The following operation can be similar to the operation of the radiation imaging system 10 described above.

Figure 3:
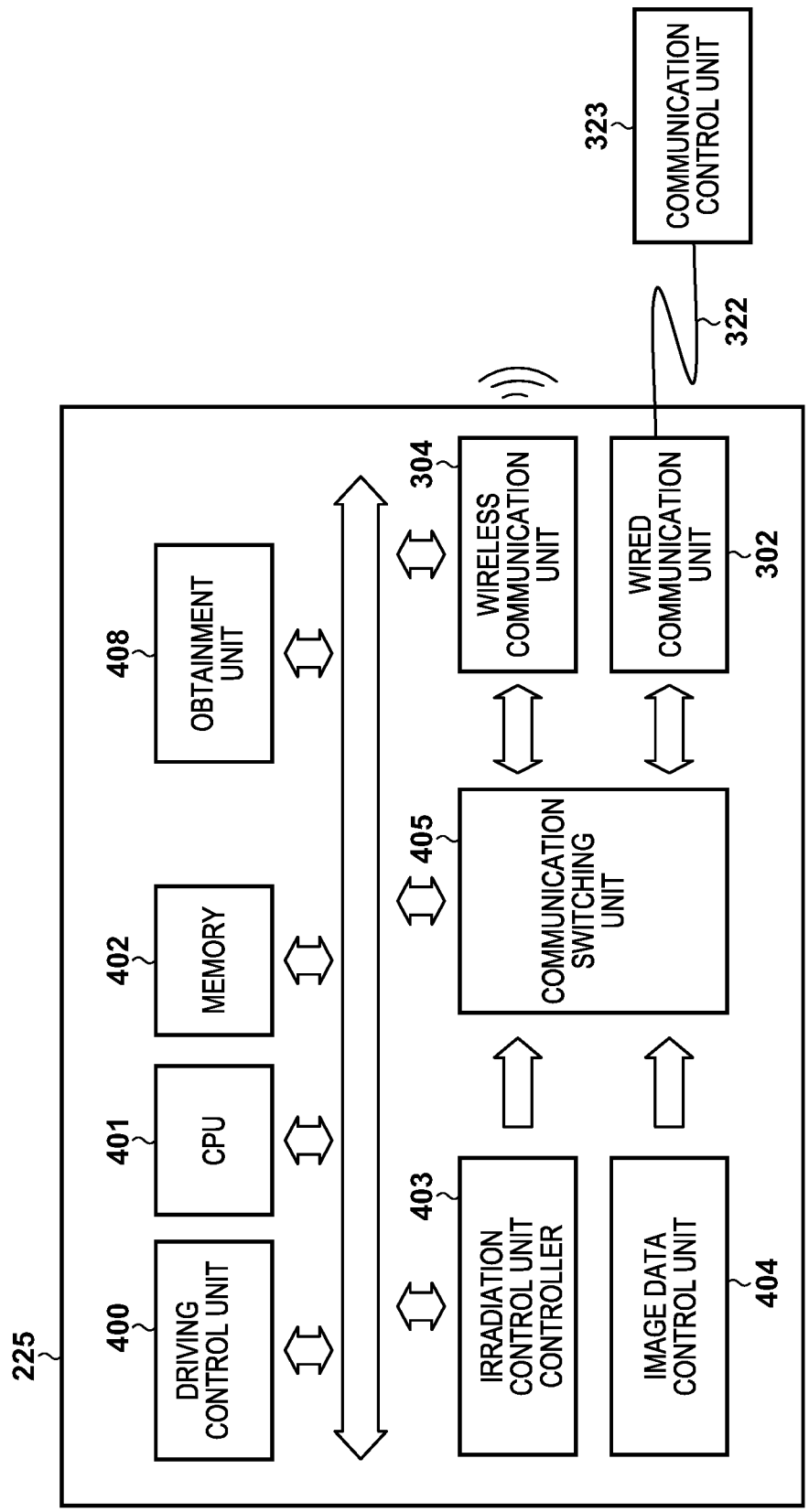
FIG. 3 is a block diagram showing an example of the arrangement of an imaging control unit of the imaging unit of the radiation imaging system of FIG. 1.

FIG. 3 is a block diagram showing an example of the arrangement of the imaging control unit 225 of the imaging unit 300. As shown in FIG. 3, the imaging control unit 225 includes a driving control unit 400, a CPU (Central Processing Unit) 401, a memory 402, an irradiation control unit controller 403, an image data control unit 404, a communication switching unit 405, the wireless communication unit 304, and the wired communication unit 302. The imaging control unit 225 also includes an obtainment unit 408 for obtaining the delay time of communication between the imaging unit 300 and the irradiation control unit.

The driving control unit 400 controls, based on the information from the signal processing unit 224 and the commands input from the system control unit 310, the driving circuit 221, the driving circuit 241, and the readout circuits 222 and 242. The CPU 401 uses the programs and various kinds of data stored in the memory 402 to control the overall imaging unit 300. The memory 402 stores, for example, programs and various kinds of data used by the CPU 401 to execute processing. In addition, the memory 402 can store various kinds of data and the radiation image data obtained by the processing performed by the CPU 401.

The irradiation control unit controller 403 controls the communication with the irradiation control unit 324 based on the information from the signal processing unit 224 and the information from the driving control unit 400. The irradiation control unit controller 403 and the irradiation control unit 324 exchange pieces of information (for example, the start of radiation irradiation, the stop notification, the real-time irradiation dose of radiation, the cumulative irradiation dose, and the like) related to the control of the radiation source 325.

The image data control unit 404 stores the radiation image data output from the readout circuit 222 in the memory 402 and controls the communication with the system control unit 310. The image data control unit 404 and the system control unit 310 exchange the radiation image data and the information (for example, control commands and the like) related to control.

As shown in FIG. 3, in a case in which the imaging unit 300 and the communication control unit 323 are connected by a communication cable 322, the communication switching unit 405 enables communication performed via the wired communication unit 302. Also, in a case in which the communication cable 322 is disconnected from the imaging unit 300, the communication switching unit 405 enables communication performed via the wireless communication unit 304 so that the imaging unit 300 and the communication control unit 323 will be connected via the wireless communication unit 304 and the access point 320. In this manner, the communication switching unit 405 appropriately switches between the wireless communication unit 304 and the wired communication unit 302 in accordance with the state.

Figure 4:
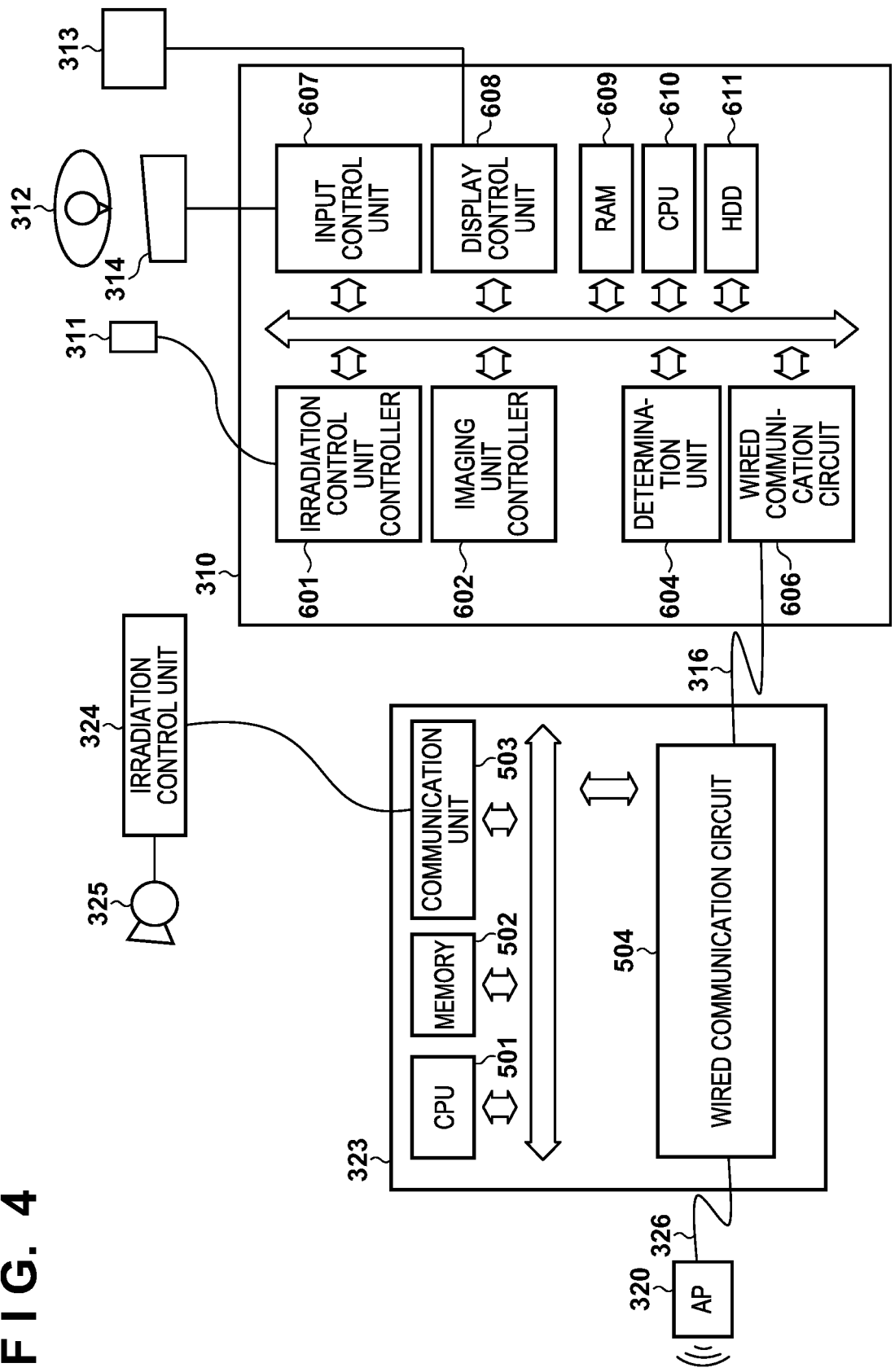
FIG. 4 is a view showing an example of the arrangement of a system control unit and a communication control unit of the radiation imaging system of FIG. 1.

FIG. 4 is a view showing an example of the arrangement of the communication control unit 323 and the system control unit 310. The communication control unit 323 includes a CPU 501, a memory 502, a communication unit 503, and a wired communication circuit 504.

The CPU 501 uses programs and various kinds of data stored in the memory 502 to control the overall communication control unit 323. The memory 502 stores, for example, the programs and the various kinds of data used by the CPU 501 to execute processing. The memory 502 can also store communication data and various kinds of data obtained by the processing of the CPU 501. The communication unit 503 communicates with the irradiation control unit 324 based on instructions from an irradiation control unit controller 601 of the system control unit 310 and the irradiation control unit controller 403 of the imaging unit 300. The wired communication circuit 504 enables communication with the access point 320, the imaging unit 300 connected by wired communication via the communication cable 322, and each component of the system control unit 310. For example, the wired communication circuit has a switching hub function.

The system control unit 310 includes the irradiation control unit controller 601, an imaging unit controller 602, a wired communication circuit 606, an input control unit 607, a display control unit 608, a RAM (Random Access Memory) 609, a CPU 610, a storage unit 611, and a determination unit 604.

The irradiation control unit controller 601 performs, based on an instruction from the operator 312, control related to radiation generation in the radiation source 325 via the irradiation control unit 324. The imaging unit controller 602 performs, based on an instruction from the operator 312, control related to capturing a radiation image on the imaging unit 300. The wired communication circuit 606 is in charge of communicating various kinds of data and various kinds of information from the system control unit 310 to the communication control unit 323 via the room-to-room communication cable 316. For example, in a case in which the input unit 314 is a touch panel, the input control unit 607 performs various kinds of control related to the input unit 314 such as switching the display of the input unit 314 in accordance with the operation made on the input unit 314 by the operator 312. The display control unit 608 performs various kinds of control processes related to display on the display unit 313. The RAM 609 temporarily stores various kinds of data and various kinds of information required for the processing by the system control unit 310. The CPU 610 uses programs and various kinds of data stored in the RAM 609 to control the overall system control unit 310. The storage unit 611 is formed, for example, by a hard disk or the like and stores various kinds of programs, various kinds of data and information, and the like. Although it will be described in detail later, the determination unit 604 determines whether to permit imaging by exposure control using the signal output from each detection unit, as described above, based on the radiation irradiation conditions set by the operator and the information related to the communication delay time obtained by the obtainment unit 408. That is, the determination unit 604 makes an AEC execution determination based on these pieces of information.

Figure 5:
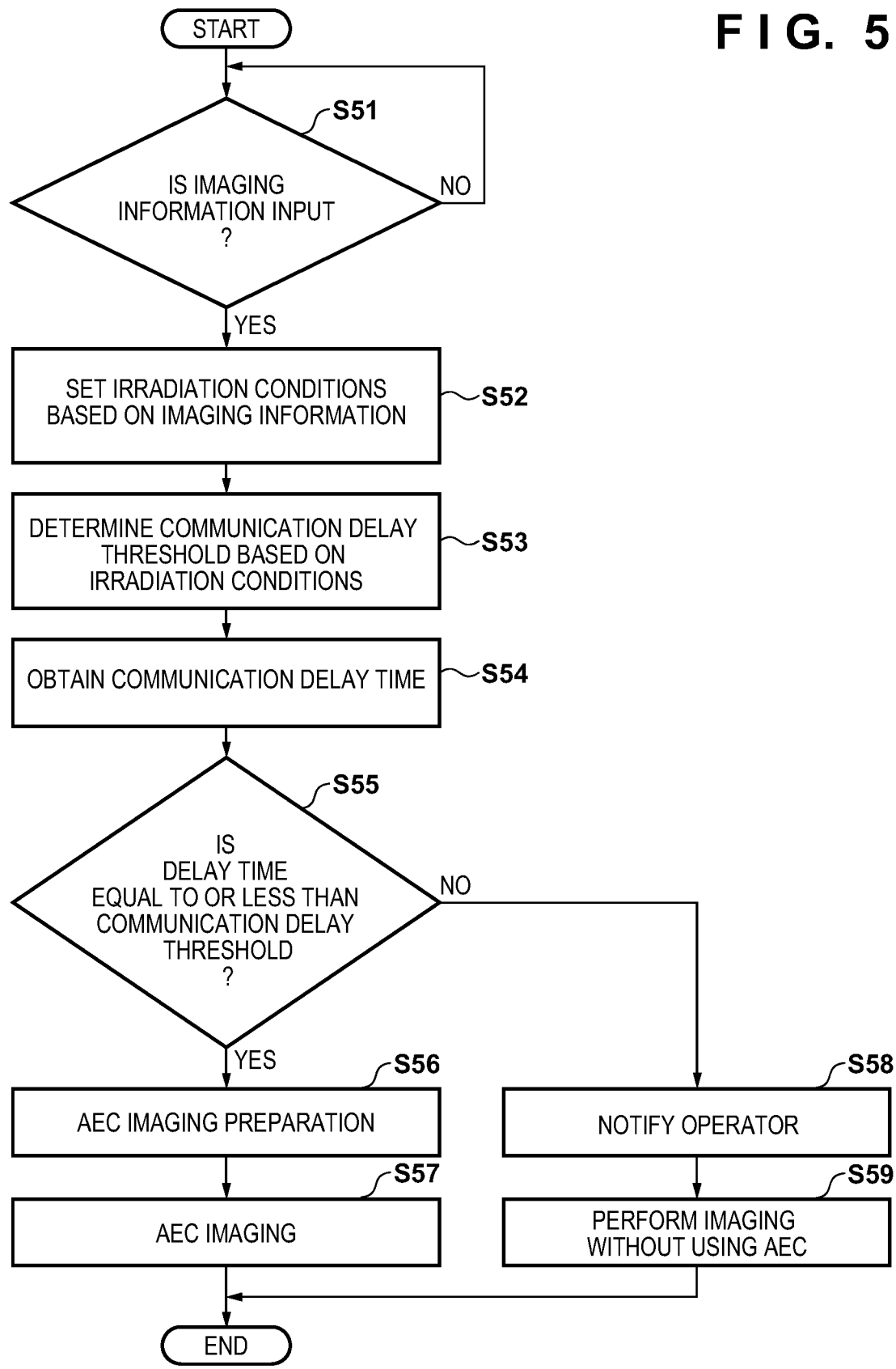
FIG. 5 is a flowchart showing the sequence of an AEC execution determination operation in the radiation imaging system of FIG. 1.

The control method of the radiation imaging system 10 including an AEC execution determination operation according to this embodiment will be described next with reference to the flowchart of FIG. 5.

First, in step S51, the operator 312 inputs imaging information such as the radiation detection region (ROI), the imaging part, and the like in the system control unit 310. When the imaging information is input to the system control unit 310, the process advances to step S52.

In step S52, the system control unit 310 sets the irradiation conditions based on the imaging information such as the imaging part and the like set by the operator 312. It can be said that the radiation irradiation conditions have been set by the operator 312 since these conditions have been set based on the imaging information input by the operator 312. FIG. 6 is a table showing an example of the combinations of the imaging parts and the irradiation conditions (the tube voltage, the tube current, the irradiation time, the mAs value, and the SID (Source Image receptor Distance)). In each imaging condition, a standard value has been determined for each imaging part and the physique of the subject 306, and these values may be stored in advance in the irradiation control unit 324 and the storage unit 611 of the system control unit 310. In this embodiment, the system control unit 310 obtains, based on the imaging condition input by the operator 312, the standard values of the irradiation conditions stored in advance in the memory of the irradiation control unit 324 and the storage unit 611 of the system control unit 310. When the irradiation conditions have been obtained by the system control unit 310, the process advances to step S53.

Also, in step S51, the operator 312 may directly input the radiation irradiation conditions in the system control unit 310. In this case, the process of step S52 need not be performed. Also, if the operator 312 has input the radiation irradiation conditions in the system control unit 310 in step S51, the determination unit 604 of the system control unit 310 may determine, in step S52, whether there is a large difference between the input values and the standard values. For example, in a case in which the mAS value of the radiation irradiation conditions input by the operator 312 is 1.5 times or more than the standard value of mAs value (standard mAs value) or is 0.5 times or less than the standard value of mAs value (standard mAs value), the determination unit 604 will determine that the input value differs largely from the standard value. Subsequently, the determination unit 604 notifies the operator 312 that the input value greatly differs from the standard value via the display unit 313. Hence, the display unit 313 can also be referred to as a notification unit. If it is determined that the input value differs largely from the standard value, the process can advance to the next step S53 after the operator 312 inputs the irradiation conditions again or when the operator 312 confirms that the input value differs largely from the standard value.

In step S53, the determination unit 604 of the system control unit 310 determines a communication delay threshold based on the irradiation conditions set in step S52. The communication delay threshold is determined, for example, in accordance with the standard value of the irradiation time (standard irradiation time). As a more specific example, a value which is 5% of the standard value of irradiation time (standard irradiation time) set for each imaging part shown in FIG. 6 is set as the communication delay threshold. For example, in a case in which a chest PA (Posterior-Anterior view) is to be captured, 5% of 10 ms set as the standard irradiation time, that is, 0.5 ms is set as the communication delay threshold, and irradiation time up to 10.5 ms is permitted. Each communication delay threshold shown in FIG. 6 is obtained by calculating 5% of the standard irradiation time of each imaging part as the communication delay threshold.

Next, when the communication delay threshold has been determined, the system control unit 310 causes, in step S54, the obtainment unit 408 to obtain the communication delay time between the imaging unit 300 and the irradiation control unit 324. First, the system control unit 310 transmits, to the imaging unit 300, a command for measuring the communication delay time. Upon receiving the command for measuring the communication delay time, the obtainment unit 408 of the imaging unit 300 transmits a packet for measuring the delay time to the irradiation control unit 324 in accordance with the control of the CPU 401. Upon receiving the packet for measuring the delay time, the irradiation control unit 324 transmits a response to the packet to the obtainment unit 408 of the imaging unit 300. That is, the obtainment unit 408 of the imaging unit 300 obtains the communication delay time by causing the packet for measuring the delay time to be reciprocated between the imaging unit 300 and the irradiation control unit 324 and measuring the reciprocation time of the packet.

Since the one-way communication time from the imaging unit 300 to the irradiation control unit 324 can be assumed to be half the packet reciprocation time, time corresponding to half the measured communication reciprocation time will be communication delay time. As a response to the command for measuring the communication delay time, the imaging unit 300 transmits the delay time obtained by the obtainment unit 408 to the system control unit 310.

The reciprocation time of a packet may vary depending on the communication environment. Hence, the obtainment unit 408 can measure the packet reciprocation time a plurality of times and obtain, as the communication delay time, the maximum value, the average value, or the mode obtained as a result of measuring the reciprocation time of the packet a plurality of times.

Next, in step S55, the determination unit 604 of the system control unit 310 compares the communication delay time obtained in step S54 and the communication delay threshold determined in step S53. Based on the result of the comparison, the determination unit 604 determines whether to permit imaging by exposure control using the signal output from each detection unit (the pixel 121). If the delay time is equal to or less than the communication delay threshold, the determination unit 604 will determine that imaging by exposure control using the signal output from each detection unit (the pixel 121) can be permitted, and the process advances to step S56. On the other hand, if the delay time is larger than the communication delay threshold, the determination unit 604 will determine that imaging by exposure control using the signal output from each detection unit (the pixel 121) cannot be permitted, and the process advances to step S58. Although the delay time and the communication delay threshold were compared in this embodiment, in a case in which the stop timing is to be predicted from the cumulative irradiation dose, the standard irradiation time and the sum of obtained delay time and the time required to make a prediction obtain a high prediction accuracy may be compared.

When imaging by exposure control is permitted by the determination unit 604, the system control unit 310 causes, in step S56, the imaging unit 300 to perform AEC imaging preparation. More specifically, the system control unit 310 will transmit, to the imaging unit 300, an AEC imaging preparation command and information necessary for imaging by AEC such as the radiation detection region (ROI), the imaging information such as the imaging part, the radiation irradiation conditions, and the like. Upon receiving the information necessary to execute imaging by AEC, the imaging unit 300 calculates the appropriate dose to determine the radiation irradiation stop timing. In addition, upon receiving the AEC imaging preparation command, the imaging unit 300 shifts to an AEC imaging preparation state in which radiation imaging by AEC can be performed. Furthermore, the system control unit 310 transmits the irradiation conditions to perform imaging by AEC to the irradiation control unit 324.

Next, in step S57, the AEC imaging preparation is completed in the imaging unit 300 and the irradiation control unit 324, and radiation is emitted from the radiation source 325 when the radiation irradiation switch 311 is pressed by the operator 312. The imaging unit 300 detects the radiation that passed through the subject 306 and entered the radiation detection region (ROI) and calculates the cumulative irradiation dose. Based on the cumulative irradiation dose and the appropriate dose calculated in step S56, the imaging unit 300 transmits a notification to the irradiation control unit 324 to stop the radiation irradiation.

The irradiation control unit 324 causes the radiation source 325 to stop radiation irradiation based on the radiation irradiation stop timing of the notification. At this time, the radiation irradiation stop timing can be controlled so that the radiation irradiation will be stopped at an appropriate timing considering the communication delay time from the imaging unit 300 to the irradiation control unit 324.

Although the imaging unit 300 performs radiation irradiation stop notification as a detection result of detecting radiation in this embodiment, the present invention is not limited to this. It may be arranged so that the imaging unit 300 will transmit the total dose as a detection result to the irradiation control unit 324 for each predetermined time and the irradiation control unit 324 will calculate the cumulative value of the total doses.

On the other hand, in step S55 as described above, if the determination unit 604 determines that imaging by exposure control using the signal output from each detection unit (the pixel 121) cannot be permitted, the process advances to step S58. In step S58, the system control unit 310 causes, via the display control unit 608, the display unit 313 (the notification unit) to display a message that imaging by exposure control cannot be performed to notify (warn) the operator 312. At this time, the system control unit 310 does not transmit the AEC imaging preparation command and the information necessary for imaging by AEC to the imaging unit 300.

Next, in step S59, the operator 312 confirms that imaging by exposure control cannot be performed and operates the system control unit 310 via the input unit 314 or the like. In accordance with the instruction (operation) of the operator 312, the radiation imaging system 10 performs imaging based on the radiation irradiation conditions set by the operator 312 in steps S51 and S52. More specifically, in step S59, based on the standard values of the irradiation conditions obtained in step S52, the system control unit 310 sets the irradiation conditions of the irradiation control unit 324 to an imaging condition which does not use AEC, that is, sets the irradiation conditions to those of a normal imaging condition with a fixed radiation irradiation time. In addition, the system control unit 310 transmits a normal imaging preparation command with the fixed radiation irradiation time to the imaging unit 300. Upon receiving the normal imaging preparation command, the imaging unit 300 shifts to a normal imaging preparation state in which radiation imaging can be performed by a fixed irradiation time. After the imaging preparation is completed in the imaging unit 300 and the irradiation control unit 324 and the operator 312 presses the radiation irradiation switch 311, radiation is emitted from the radiation source 325, and normal imaging with a fixed irradiation time is performed by using the standard values of the irradiation conditions set in accordance with the imaging part or the like.

In this embodiment, the radiation imaging system 10 switches to an imaging condition that does not use AEC when the measured communication delay time is larger than the communication delay threshold. As a result, in a case in which a large communication delay which cannot be permitted occurs due to the communication environment, it is possible to suppress an excessive radiation irradiation from being performed on the subject 306.

Also, although a value obtained by reciprocating a packet between the imaging unit 300 and the irradiation control unit 324 and measuring the reciprocation time is used as the delay time in this embodiment, the method of obtaining the delay time is not limited to this. For example, the wireless communication unit 304 will measure the data rate, the signal-to-noise ratio (SNR), the received signal strength (RSSI), and the like of the wireless communication which are the parameters indicating the wireless communication environment of the used frequency band. The obtainment unit 408 may obtain the delay time based on at least one parameter among these wireless communication environment parameters. For example, in a case in which the data rate is 150 Mbps, the communication delay time can be set as 0.4 ms. In a case in which the data rate is 10 Mbps, communication delay time can be set as 6 ms. In addition, for example, in a case in which the SNR is equal to or more than 60 dB, the communication delay time can be set as 0.4 ms. In a case in which the SNR is equal to or less than 20 dB, the communication delay threshold can be set as 6 ms. In a case in which the SNR is less than 60 dB and is larger than 20 dB, the communication delay time can be set as 2 ms. In addition, for example, in a case in which the RSSI is equal to or larger than −20 dBm, the communication delay time can be set as 0.4 ms. In a case in which the RSSI is equal to or less than −60 dBm, the communication delay time can be set as 6 ms. In a case in which the RSSI is −20 dBm and is larger than −60 dBm, the communication delay time can be set as 2 ms. The wireless communication environment parameters can be information held (measured) constantly by the wireless communication unit 304. Hence, the obtainment unit 408 can obtain the delay time by causing a packet to reciprocate between the imaging unit 300 and the irradiation control unit 324 without actually performing measurement. Hence, it becomes possible to immediately perform AEC execution determination without making the operator 312 wait.

In addition, although this embodiment described an example of an arrangement in which the communication performed between the imaging unit 300 and the irradiation control unit 324 via the communication control unit 323 includes wireless communication between the imaging unit 300 and the access point 320, the present invention is not limited to this. It may be arranged so that the imaging unit 300 and the communication control unit 323 are connected by the communication cable 322 and that the communication between the imaging unit 300 and the irradiation control unit 324 will be entirely performed by wired communication. Even in a wired communication environment, the communication delay time may increase when a device such as a switching hub or the like is interposed between the communication paths or when a communication amount on the same network has increased. Hence, in a similar manner to the case using wireless communication, the communication delay time measured in the wired communication environment is compared with the communication delay threshold determined from the radiation irradiation conditions set by the operator 312. In a case in which the delay time is larger than the communication delay threshold, the imaging condition can be switched to the imaging condition which does not use AEC so that excessive radiation irradiation on the subject can be suppressed when a communication delay of an impermissible size occurs due to the communication environment.

Furthermore, although this embodiment described an example in which the obtainment unit 408 used to obtain the delay time is included in the imaging unit 300, the present invention is not limited to this. The obtainment unit 408 may be included in the communication control unit 323, the system control unit 310, or the irradiation control unit 324.

Also, although an example in which the determination unit 604 is included in the system control unit 310 has been described, the present invention is not limited to this. The determination unit 604 may be arranged in the imaging unit 300, the communication control unit 323, or the irradiation control unit 324.

Figure 7:
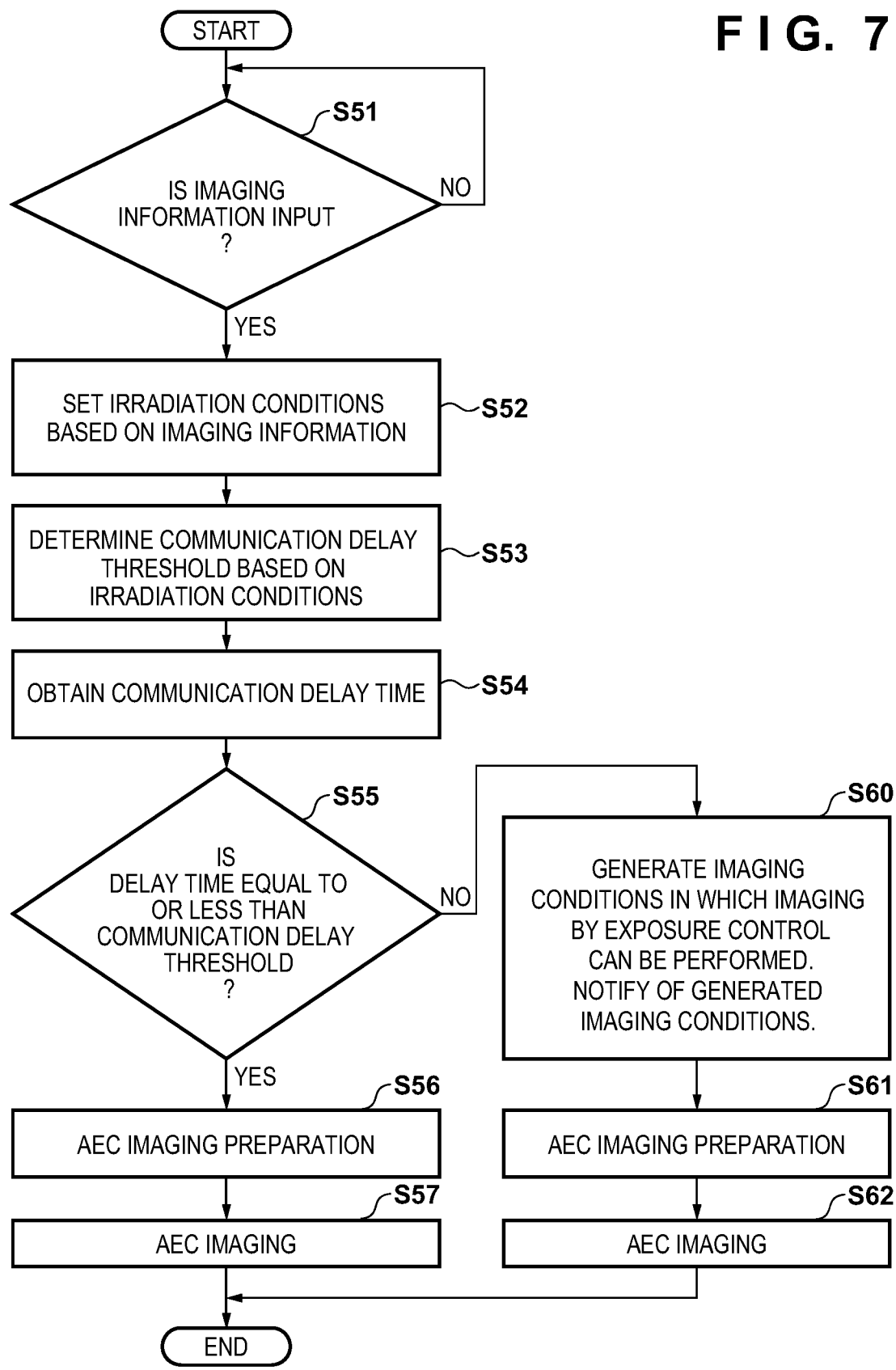
FIG. 7 is a flowchart showing the sequence of an AEC execution determination operation in a radiation imaging system of FIG. 1.

A control method of a radiation imaging system according to the second embodiment will be described with reference to FIG. 7. In the first embodiment described above, it was described that imaging will be performed by switching the imaging condition to a condition which does not use AEC and has a fixed irradiation time in a case in which the communication delay time is greater than the communication delay threshold. However, in normal imaging with a fixed irradiation time, the set irradiation conditions may not be the appropriate imaging condition for a subject 306 depending on his/her physique or the like in some cases. This embodiment will describe a method that allows, in a case in which the communication delay time is greater than the communication delay threshold and imaging by exposure control cannot be permitted, imaging using exposure control to be performed by causing the determination unit 604 to generate an imaging condition in which imaging by exposure control can be performed in the obtained delayed time. Since the arrangement and the like of a radiation imaging system 10 may be the same as those described above in the first embodiment, a description thereof will be omitted. Only differences from the first embodiment will be described. FIG. 7 is a flowchart showing the control method of the radiation imaging system 10 which includes an AEC execution determination operation according to this embodiment.

In step S55, in a case in which the delay time is greater than the communication delay threshold, the determination unit 604 will determine that imaging by exposure control using a signal output from each detection unit (each pixel 121) cannot be permitted, and the process advances to step S60. In step S60, the determination unit 604 will notify an operator 312 by causing a display unit 313 (notification unit) to display a message that imaging by exposure control cannot be performed and that a change in imaging conditions such as the radiation irradiation conditions and the like is required to perform imaging by exposure control. Furthermore, the determination unit 604 generates imaging conditions for performing imaging by exposure control and uses the display unit 313 to notify the operator 312 of the generated imaging conditions. The operator 312 confirms the displayed imaging conditions, and the radiation imaging system 10 accordingly performs imaging preparation using the generated imaging conditions.

A method of generating imaging conditions that allow imaging by exposure control to be performed in the obtained delay time will be described here. In a case in which the communication delay time is greater than the communication delay threshold, the irradiation conditions which are set by the operator 312 in steps S51 and S52 are changed so that the obtained delay time will be equal to or less than the communication delay threshold. More specifically, the standard value of the tube current (standard tube current) and the standard value of the irradiation time (standard irradiation time) are changed so the mAs value set in step S52 will not change from the value set by the operator. This will be described more specifically by using the example of imaging of a chest PA in FIG. 6. In a case in which the delay time obtained by the obtainment unit 408 in step S54 is 1.0 ms, the irradiation time corresponding to 5% (that is, the communication delay threshold) of this communication delay time is 20 ms. Since the irradiation dose (mAs value) necessary for imaging needs to be constant, the standard tube current is changed so the mAs value will not change in accordance with the change in the irradiation time from the standard irradiation time. In the example of the chest PA, the tube current will be 150 mA in a case in which the irradiation time is set to 20 ms. The mAs value at this time remains at 3.0 and does not change from that before the change in the irradiation time. By changing the irradiation time and the tube current without changing the mAs value and setting the delay time to fall within the communication delay threshold, it becomes possible to perform imaging by exposure control. The operation performed in step S61 is similar to that in step S56, and the operation performed in step S62 is similar to that in step S57.

In this embodiment, in a case in which the delay time obtained by the obtainment unit 408 is greater than the communication delay threshold determined based on the imaging part information input by the operator 312, the determination unit 604 generates imaging conditions that will allow imaging by exposure control to be performed in the obtained delay time. It becomes possible to perform imaging using AEC by changing the irradiation conditions even in a case in which a communication delay of an impermissible size has occurred due to the communication environment.

Figure 8:
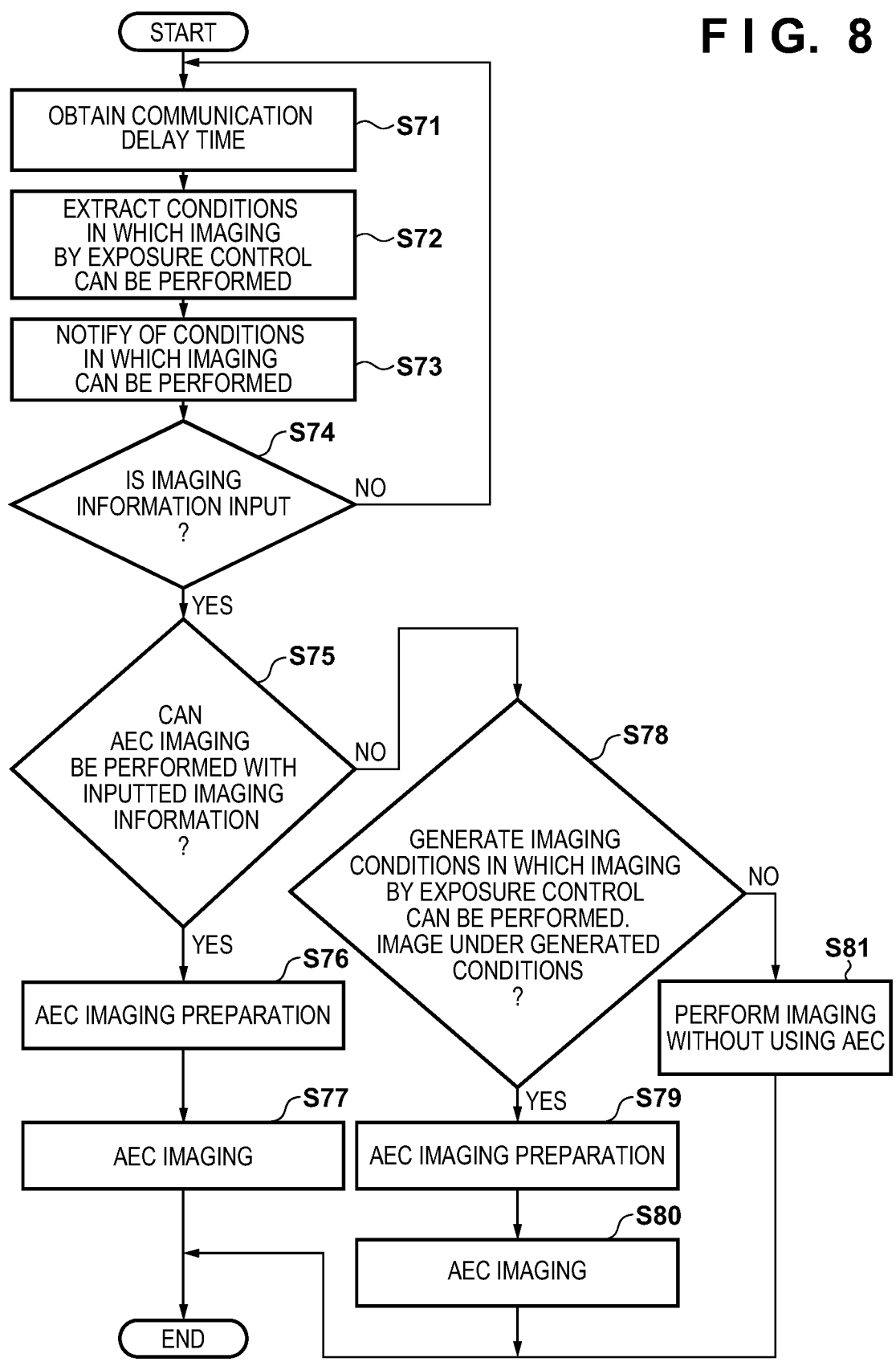
FIG. 8 is a flowchart showing the sequence of an AEC execution determination operation in a radiation imaging system of FIG. 1.

A control method of a radiation imaging system according to the third embodiment of the present invention will be described with reference to FIG. 8. The above first and second embodiments described that, after an imaging part has been set by an operator 312, imaging control using AEC will be performed after an obtainment unit 408 obtains the communication delay time. However, there may be a case in which imaging using AEC cannot be performed after irradiation conditions have been set by the operator 312 or a case in which the imaging preparation needs to be reworked (redone) due to a revelation that imaging cannot be performed under desired imaging conditions. In this embodiment, the obtainment unit 408 will periodically obtain the communication delay time, and a determination unit 604 will determine the imaging conditions that will allow imaging by exposure control using the signal output from each detection unit (each pixel 121) to be performed. Subsequently, the determination unit 604 will notify the operator 312 of imaging conditions that allow imaging by exposure control to be performed via a display unit 313 (notification unit). For example, the determination unit 604 determines in advance the imaging part that can be captured under the desired radiation irradiation conditions and notify the operator 312 of this imaging part to suppress the occurrence of a state in which the imaging preparation needs to be reworked. Since the arrangement and the like of a radiation imaging system 10 may be the same as those described above in the first embodiment, a description thereof will be omitted. Only differences from the first embodiment will be described. FIG. 8 is a flowchart showing the control method of the radiation imaging system which includes an AEC execution determination operation according to this embodiment.

First, in step S71, a system control unit 310 causes the obtainment unit 408 to obtain the communication delay time between an imaging unit 300 and an irradiation control unit 324. The method used to obtain the delay time is the same as that in step S54 described above.

Next, in step S72, the determination unit 604 of the system control unit 310 compares the communication delay time obtained in step S71 with the communication delay threshold indicated in the irradiation condition combination shown in FIG. 6, and extracts a condition (imaging part) in which imaging can be performed. For example, in a case in which the delay time is 1.0 ms, the determination unit 604 will determine that the front of the abdomen, the side of the abdomen, and the four limbs, each of which is an imaging part whose communication delay threshold is greater than 1.0 ms, are conditions in which imaging can be performed and extracts the conditions. In other words, the determination unit 604 determines that imaging by exposure control can be permitted because the delay time is equal to or less than the communication delay threshold in the radiation irradiation conditions used in the imaging of each of the front of the abdomen, the side of the abdomen, and the four limbs, and extracts these imaging parts. Also, in step S73, the determination unit 604 of the system control unit 310 notifies the operator 312 by causing a display unit 313 (notification unit) to display the imaging parts, which were determined to be imageable and extracted in step S72, as parts that can be imaged by exposure control.

In step S74, when imaging information such as the imaging part and the like is input to the system control unit 310 by the operator 312, the process advances to step S75. In step S75, if there is no input from the operator 312 for a predetermined time, the process will return to step S71, and the obtainment unit 408 will reobtain the delay time. In this manner, the obtainment unit 408 periodically obtains the communication delay time between the imaging unit 300 and the irradiation control unit 324.

In step S75, the determination unit 604 of the system control unit 310 determines whether the irradiation conditions corresponding to the imaging information input by the operator 312 are the irradiation conditions that allow imaging by exposure control and are extracted in step S72. If it is determined that the irradiation conditions set by the operator 312 are the conditions determined to be capable of imaging by exposure control extracted in step S72, that is, in other words, if it is determined that the irradiation conditions are conditions in which imaging by exposure control can be permitted by the determination unit 604, the process advances to step S76. The operation performed in step S76 is similar to that in step S56, and the operation performed in step S77 is similar to that in step S57.

In step S75, if imaging by exposure control is not permitted by the determination unit 604, the process advances to step S78. In step S78, the determination unit 604 notifies the operator 312 by causing, in a similar manner to the operation performed in step S60, the display unit 313 (the notification unit) to display a message that imaging by exposure control cannot be performed and that imaging conditions such as the radiation irradiation conditions and the line need to be changed to perform imaging by exposure control. Furthermore, the determination unit 604 generates, in a similar manner to the operation performed in step S60, imaging conditions for performing imaging by exposure control and uses the display unit 313 to notify the operator 312 of the generated imaging conditions. In addition, in step S78, the determination unit 604 of system control unit 310 causes the display unit 313 to display options such as whether imaging using exposure control is to be performed by changing the imaging condition and whether imaging is to be performed by not using exposure control, and prompts the operator 312 to make a selection.

If the operator 312 selects the option to perform imaging using exposure control by changing the imaging conditions, the radiation imaging system 10 will advance to step S79 in accordance with this selection. The operation performed in step S79 is similar to that in step S61, and the operation performed in step S80 is similar to that in step S62. Also, if the operator 312 selects the option to perform imaging without using exposure control, the radiation imaging system 10 will advance to step S81 in accordance with this selection. The operation performed in step S81 is similar to that in step S59.

In this embodiment, the obtainment unit 408 periodically obtains the communication delay time between the imaging unit 300 and the irradiation control unit 324. The determination unit 604 extracts the imaging conditions in which imaging by exposure control using each detection unit (each pixel 121) can be performed, and notifies, via the display unit 313 (notification unit), the operator 312 of the imaging conditions in which imaging by exposure control can be performed. As a result, it is possible to suppress the occurrence of a state in which the imaging preparation needs to be reworked and the like.

The solution described above provides a technique advantageous in improving the controllability of AEC in a radiation imaging system.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging system comprising:
an imaging unit including a plurality of pixels configured to generate a radiation image and a detection unit configured to detect incident radiation to perform exposure control;
an irradiation control unit configured to control radiation irradiation by a radiation source, an obtainment unit configured to obtain a delay time of communication between the imaging unit and the irradiation control unit; and
a determination unit,
wherein
the determination unit determines, based on a radiation irradiation condition set by an operator and the delay time obtained by the obtainment unit, whether to permit imaging by exposure control using a signal output from the detection unit.

2. The radiation imaging system according to claim 1, wherein the irradiation condition includes a standard irradiation time, and
the determination unit determines a communication delay threshold in accordance with the standard irradiation time, and permits the imaging by exposure control in a case in which the delay time is not more than the communication delay threshold.

3. The radiation imaging system according to claim 1, wherein the radiation imaging system further includes a notification unit, and
in a case in which the imaging by exposure control cannot be permitted, the determination unit notifies, via the notification unit, the operator that the imaging by exposure control cannot be performed.

4. The radiation imaging system according to claim 3, wherein in a case in which the determination unit determines that the imaging by exposure control cannot be permitted, the radiation imaging system will perform, after causing the notification unit to notify, via the notification unit, the operator that the imaging by exposure control cannot be performed, imaging by a radiation irradiation condition set by the operator in accordance with an instruction of the operator.

5. The radiation imaging system according to claim 1, wherein the radiation imaging system further includes a notification unit, and
in a case in which the imaging by exposure control cannot be permitted, the determination unit generates an imaging condition in which the imaging by exposure control can be performed in the delay time and causes the notification unit to notify the operator that the imaging by exposure control cannot be performed and of the generated imaging condition.

6. The radiation imaging system according to claim 2, wherein the radiation imaging system further includes a notification unit, and
the irradiation condition further includes a standard tube current, and
in case in which the imaging by exposure control cannot be permitted, the determination unit generates an imaging condition in which the imaging by exposure control can be performed by changing the standard tube current and the standard irradiation time so a mAs value will not change from a value set by the operator, and the determination unit causes the notification unit to notify the operator that the imaging by exposure control cannot be performed and of the generated imaging condition.

7. The radiation imaging system according to claim 5, wherein in a case in which the determination unit determines that the imaging by exposure control cannot be permitted, the radiation imaging system will perform, after causing the notification unit to notify, via the notification unit, the operator that the imaging by exposure control cannot be performed, imaging by the generated imaging condition or imaging by a radiation irradiation condition set by the operator in accordance with an instruction of the operator.

8. The radiation imaging system according to claim 3, wherein the obtainment unit periodically obtains the delay time, and the determination unit determines a condition in which the imaging by exposure control can be performed and causes the notification unit to notify the operator of the condition in which the imaging by exposure control can be performed.

9. The radiation imaging system according to claim 1, wherein the communication between the imaging unit and the irradiation control unit includes wireless communication.

10. The radiation imaging system according to claim 1, wherein the communication between the imaging unit and the irradiation control unit is entirely performed by wired communication.

11. The radiation imaging system according to claim 1, wherein the obtainment unit obtains the delay time by causing a packet for measuring the delay time to be reciprocated between the imaging unit and the irradiation control unit and by measuring a reciprocation time of the packet.

12. The radiation imaging system according to claim 11, wherein the obtainment unit measures the reciprocation time of the packet for a plurality of times, and obtains, as the delay time, one of a maximum value, an average value, and a mode obtained as a result of measuring the reciprocation time of the packet for the plurality of times.

13. The radiation imaging system according to claim 9, wherein the obtainment unit obtains the delay time based on at least one of parameters including a data rate, a signal-to-noise ratio, and a received signal strength of the wireless communication.

14. The radiation imaging system according to claim 1, wherein the imaging unit includes a pixel region in which the plurality of pixels are arranged, and the detection unit is arranged in the pixel region.

15. The radiation imaging system according to claim 14, wherein one of the plurality of pixels functions as the detection unit.

16. The radiation imaging system according to claim 1, wherein the imaging unit includes a pixel region in which the plurality of pixels are arranged, and the detection unit is arranged outside the pixel region.

17. A control method of a radiation imaging system that includes an imaging unit including a plurality of pixels configured to generate a radiation image and a detection unit configured to detect incident radiation to perform exposure control, an irradiation control unit configured to control radiation irradiation by a radiation source, and an obtainment unit configured to obtain a delay time of communication between the imaging unit and the irradiation control unit, the control method comprising:

a step of determining, based on a radiation irradiation condition set by an operator and the delay time obtained by the obtainment unit, whether to permit imaging by exposure control using a signal output from the detection unit.

18. A non-transitory computer-readable storage medium storing a program for causing a computer to execute a control method of a radiation imaging system that includes an imaging unit including a plurality of pixels configured to generate a radiation image and a detection unit configured to detect incident radiation to perform exposure control, an irradiation control unit configured to control radiation irradiation by a radiation source, and an obtainment unit configured to obtain a delay time of communication between the imaging unit and the irradiation control unit, the control method comprising:

a step of determining, based on a radiation irradiation condition set by an operator and the delay time obtained by the obtainment unit, whether to permit imaging by exposure control using a signal output from the detection unit.

* * * * *